United States Patent
Kano et al.

[11] Patent Number: 5,118,840
[45] Date of Patent: Jun. 2, 1992

[54] METHOD OF CRYSTALLIZING PHENYLALANINE

[75] Inventors: Mikiya Kano; Shinji Fujita; Tadashi Takemoto; Toshihisa Kato; Naoko Sugiyama, all of Kawasaki, Japan

[73] Assignee: Ajinomoto Co., Inc., Tokyo, Japan

[21] Appl. No.: 729,168

[22] Filed: Jul. 12, 1991

[30] Foreign Application Priority Data

Aug. 3, 1990 [JP] Japan .................. 2-206500
Aug. 23, 1990 [JP] Japan .................. 2-222093

[51] Int. Cl.$^5$ ............................. C07C 229/00
[52] U.S. Cl. ............................. 562/443; 560/41
[58] Field of Search ................. 562/443; 560/41

[56] References Cited

U.S. PATENT DOCUMENTS 4,661,606  4/1987  Tuominen et al. ............ 562/443
4,731,469  3/1988  Evans et al. .................. 562/443

Primary Examiner—Bruce Gray
Attorney, Agent, or Firm—Oblon, Spivak, McClelland, Maier & Neustadt

[57] ABSTRACT

A method of crystallizing phenylalanine in the form of $\alpha$-crystals at a temperature below $\alpha \to \beta$ transition temperature comprises:

forming an aqueous solution of phenylalanine at a temperature above the $\alpha \to \beta$ transition temperature, the aqueous solution of phenylalanine including:

(1) a specified amount of NaCl, or
(2) $NH_4Cl$ and a small amount of a surfactant; and cooling the solution below the $\alpha \to \beta$ transition temperature.

5 Claims, 6 Drawing Sheets

METHOD OF CRYSTALLIZING PHENYLALANINE

BACKGROUND OF THE INVENTION

1. Field of the Invention

This invention relates to a method of separating α-crystals of phenylalanine.

2. Description of the Prior Art

Phenylalanine is an essential amino acid (a vital nutrient) and is also a substance of industrial importance useful as a raw material for the production of L-aspartyl-L-phenylalanine methyl ester, a sweetener.

Phenylalanine may be obtained by isolation from a hydrolyzate of protein, such as defatted soybeans, by fermentation or by organic synthesis; and crystallization is generally adopted as the method of purification in any of these processes. Optically active phenylalanine exists as α-crystals or β-crystals, in which the α-crystals are in the form of plates or flakes, while the β-crystals are in the form of fine needles. Hence, crystallization as the α-crystal is better in the case of isolation, and gives high-quality products with less mother liquor left attached.

Phenylalanine exists in the form of α-crystals at a temperature higher than a specific level (normal transition point temperature) and in the form of β-crystals at a temperature lower than the normal transition point temperature. The normal transition point temperature of phenylalanine is about 37° C. in aqueous systems and varies in some degree depending on the crystallization system. The transition point in a specific crystallization system can be easily measured by investigation of the crystals separated from said crystallization system, such as by observation under a microscope or X-ray powder diffractometry. It was known that the normal transition point temperature generally lowers by addition of an organic solvent, but no such phenomenon was known with aqueous systems.

Thus, a need exists for the obtention of crystals of phenylalanine in the α-crystal form at temperatures below the normal transition point temperature.

SUMMARY OF THE INVENTION

It is thus an object of the present invention to provide a method of producing high-quality crystals of phenylalanine.

It is a further object of the present invention to provide a method for crystallizing phenylalanine by cooling while maintaining the phenylalanine crystals in the α-form.

These and other objects of the invention have been attained by the provision of a method of crystallizing phenylalanine in the form of α-crystals at a temperature below the normal transition point temperature of phenylalanine, said normal transition point temperature being a temperature above which phenylalanine exists in the form of α-crystals and below which phenylalanine exists in the form of β-crystals, said method comprising:

forming an aqueous solution of phenylalanine at a temperature above said normal transition point temperature, said aqueous solution of phenylalanine including:

(1) at least 20 grams of sodium chloride per 100 grams of water in said solution; or (2) ammonium chloride and a surface active agent, said surface active agent being present in an amount effective to suppress an increase in said normal transition point temperature brought about in an aqueous solution of phenylalanine by the presence of ammonium chloride in a concentration of about 20 grams per 100 grams of water in said solution; and cooling said aqueous solution of phenylalanine to a temperature below said normal transition point temperature to recover phenylalanine in said α-crystal form.

BRIEF DESCRIPTION OF THE DRAWING FIGURES

Various other objects, features and attendant advantages of the present invention will be more fully appreciated as the same becomes better understood from the following detailed description when considered in connection with the accompanying drawing figures, wherein.

DETAILED DESCRIPTION OF THE INVENTION

Figure 1:
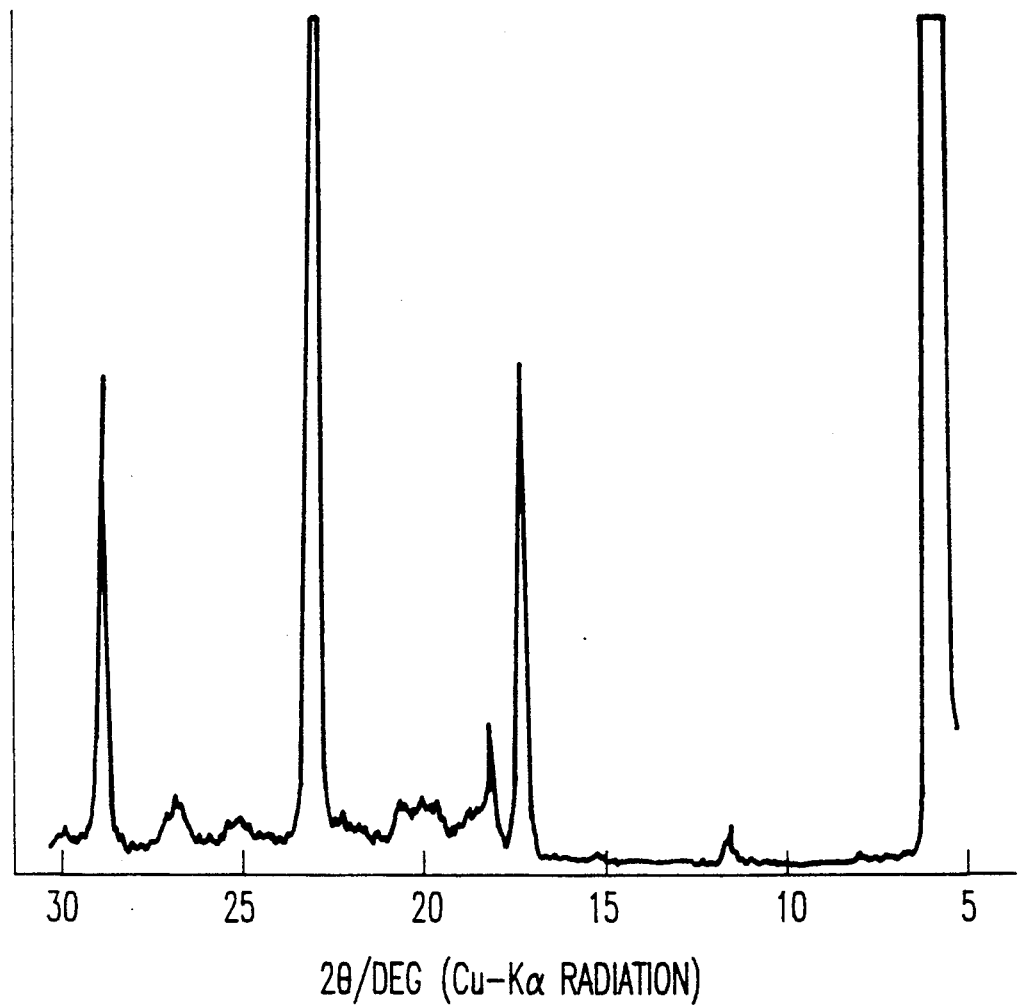
FIG. 1 is a powder X-ray spectra of the L-phenylalanine crystals obtained in Example 2.

The crystal form of phenylalanine in an aqueous system containing ammonium chloride or sodium chloride, such as solutions obtained by hydrolyzing a protein in hydrochloric acid and neutralizing with ammonia water or sodium hydroxide, was quite unknown. The present inventors made extensive investigations on this problem, and found that, when ammonia water is used for neutralization, an ammonium chloride concentration of about 20 g/100 g·water is a critical point, above which transition to β-crystals occurs even at 40° C. (increase of normal transition point temperature) and below which phenylalanine remains in the form of α-crystals at 40° C. Further studies have led to the discovery that, if a small amount of a surface-active agent is added to the solution, the transition of crystal form does not occur at an ammonium chloride concentration over the above critical point (20 g/100 g·water), thus giving phenylalanine in the form of α-crystals, even when cooled to a temperature less than 35° C.

The present inventors also discovered that, when sodium hydroxide is used for neutralization, high-quality phenylalanine in the form of α-crystals can be obtained with a high yield by increasing the sodium chloride concentration of the phenylalanine solution to a level of 20 g/100 g·water or higher and cooling to a temperature of 35° C. or lower, preferably in the range from 0° to 5° C.

This invention can be extensively applied to a variety of aqueous solutions containing phenylalanine. These include solutions obtained in the process of proteolysis (such as a hydrolyzate of protein, a solution obtained from this hydrolyzate by treatment with an ion-exchange resin or with a decolorizing resin, a solution of the crude crystals separated out from this treated hydrolyzate, and the mother liquor from which said crude crystals have been separated); solutions obtained in the process of fermentation (such as a fermented solution, a solution obtained from this fermented solution by treatment with an ion-exchange resin or with a decolorizing resin, a solution of the crude crystals separated out from this treated solution, and the mother liquor from which said crude crystals have been separated); solutions obtained in the process of organic synthesis (such as a solution obtained by reaction of DL-acetylphenylalanine with an acylase); and an HCl hydrolyzate of the mother liquor from which L-aspartyl-L-phenylalanine methyl ester (which is a sweetener) has been separated.

Various surface-active agents prove effective when used in a system containing ammonium chloride, but, non-ionic surfactants, such as sorbitan alkyl esters (e.g., "Nonion LP-20" manufactured by Nippon Oil and Fats Co., Ltd.) and polyoxyethylene-sorbitan alkyl esters (e.g., "Nonion LT-221" manufactured by Nissan Oil and Fats Co., Ltd.) were especially satisfactory. The amount of surface-active agent to be added should be sufficient to inhibit the increase of the transition point brought about by $NH_4Cl$ (20 g/100 g $H_2O$), and preferably should be in the range from 0.05 to 0.5% based on the weight of phenylalanine (a range which minimizes the amount of surface-active agent included in the separated crystals of phenylalanine and ensures sufficient suppression of the crystal form transition temperature).

The saturation concentration of phenylalanine at the time of crystallization (namely, its solubility) varies with the type of solution used. In systems containing ammonium aspartate or the like (such as a solution obtained by hydrolyzing with hydrochloric acid the mother liquor from which crystals or L-aspartyl-L-phenylalanine methyl ester has been separated, followed by neutralization with ammonia water), the rate of crystal separation can be markedly enhanced by salting-out. In addition, the transition point temperature is further lowered and phenylalanine remains in the form of α-crystal at a temperature of 0° to 5° C. in these systems.

With systems containing sodium chloride, its concentration is set at a level of 20 g100 g·water or higher by adding sodium chloride, by concentrating the solution, or by adding a sodium source and a chlorine source separately, thereby forming sodium chloride in the solution. The application of this method using high-concentration sodium chloride is not limited to an aqueous solution of phenylalanine obtained by neutralizing a protein hydrolyzate with sodium hydroxide as described above. It is applicable to any type of aqueous solution containing phenylalanine; for example, even with a solution of phenylalanine formed by fermentation containing no sodium chloride (or a treated solution thereof), the yield of objective α-crystal phenylalanine can be enhanced by addition of sodium chloride to a concentration of 20 g/100 g·water or higher.

Having generally described this invention, a further understanding can be obtained by reference to certain specific examples which are provided herein for purposes of illustration only and are not intended to be limiting unless otherwise specified.

EXAMPLES

Example 1

A mixture of 24 g ammonium chloride, 5 g L-phenylalanine and 100 g water was heated at 70° C. until a clear solution was obtained, 15 mg Nonion LT-221 was then added, the resulting solution was gradually cooled to 25° C., and the crystals which separated out were collected and washed with a small volume of water. The crystals thus obtained proved to be of α-crystal form by observation under a microscope and by powder X-ray diffractometry.

Example 2

| (Solution for Hydrolysis with HCl) | | |
|---|---|---|
| | Concn. | Amt. in 400 g |
| T—N | 3.19 M/Kg | (1.28 M) |
| L—Phe | 148 g/Kg | (59.4 g) |
| L—Asp | 124 g/Kg | (49.8 g) |
| HCl | 3.36 M/Kg | (1.34 M) |
| NH$_4$Cl | 1.40 M/Kg | (0.56 M) |

To 400 g of a solution containing L-phenylalanine of the above composition, was added 100 mg Nonion LP20, and 28% ammonia water was gradually added while maintaining the temperature at 80° C. until the pH reached 5.6, thus separating crystals of L-phenylalanine. The total amount of ammonia water added was 105 ml. After stirring the resulting mixture for two hours, it was gradually cooled to 5° C with stirring and the crystals were collected and washed with 70 ml water. The crystals thus obtained proved to be of α-crystal form.

Figure 2:
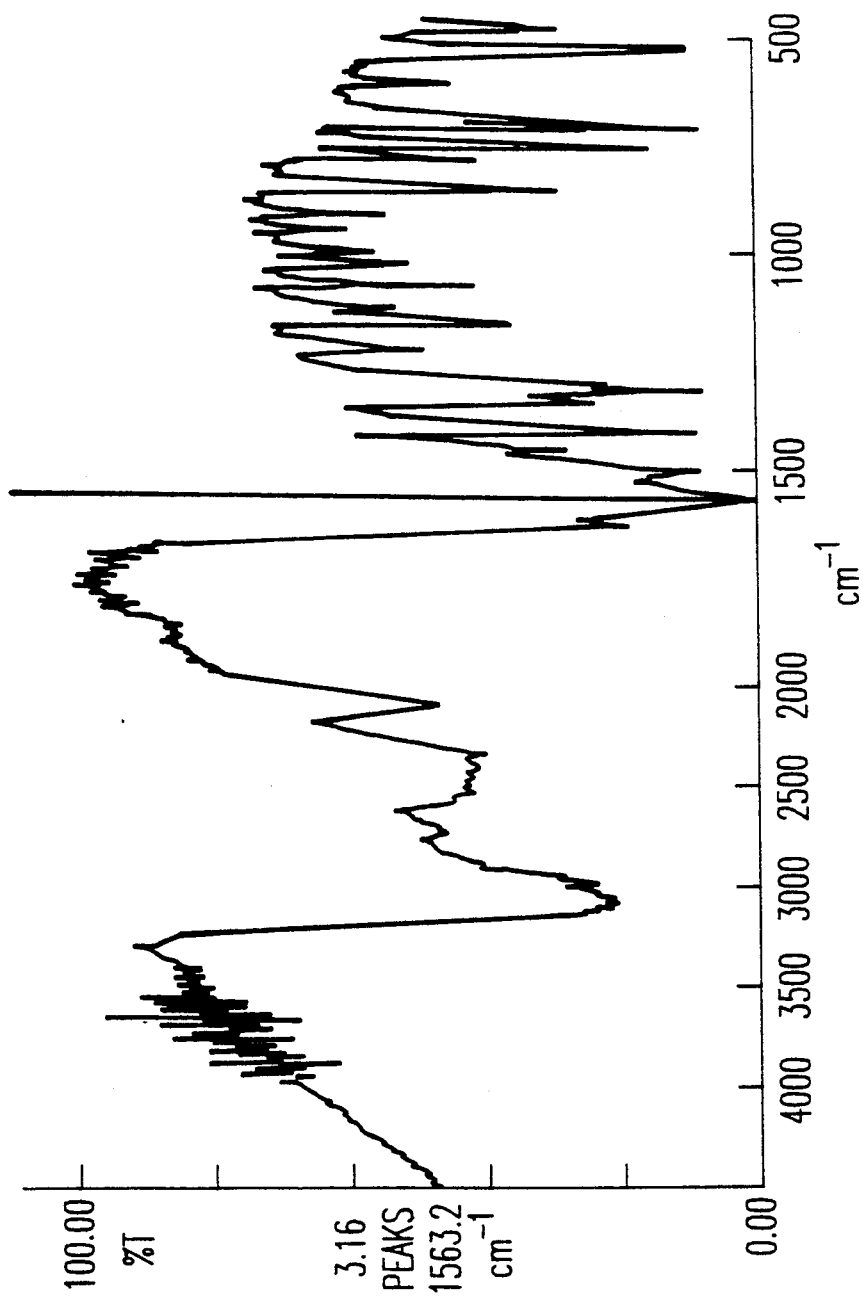
FIG. 2 is an IR spectra of the L-phenylalanine crystals obtained in Example 2.

Yield: 52.8%
Purity: 93% (measured by an amino-acid analyzer)
Rate of Crystal Separation: 85% (refer to Powder X-ray Chart FIG. 1 and IR Chart FIG. 2)
Amount of Nonion LP20 left attached: 3 ppm

Example 3

Figure 3:
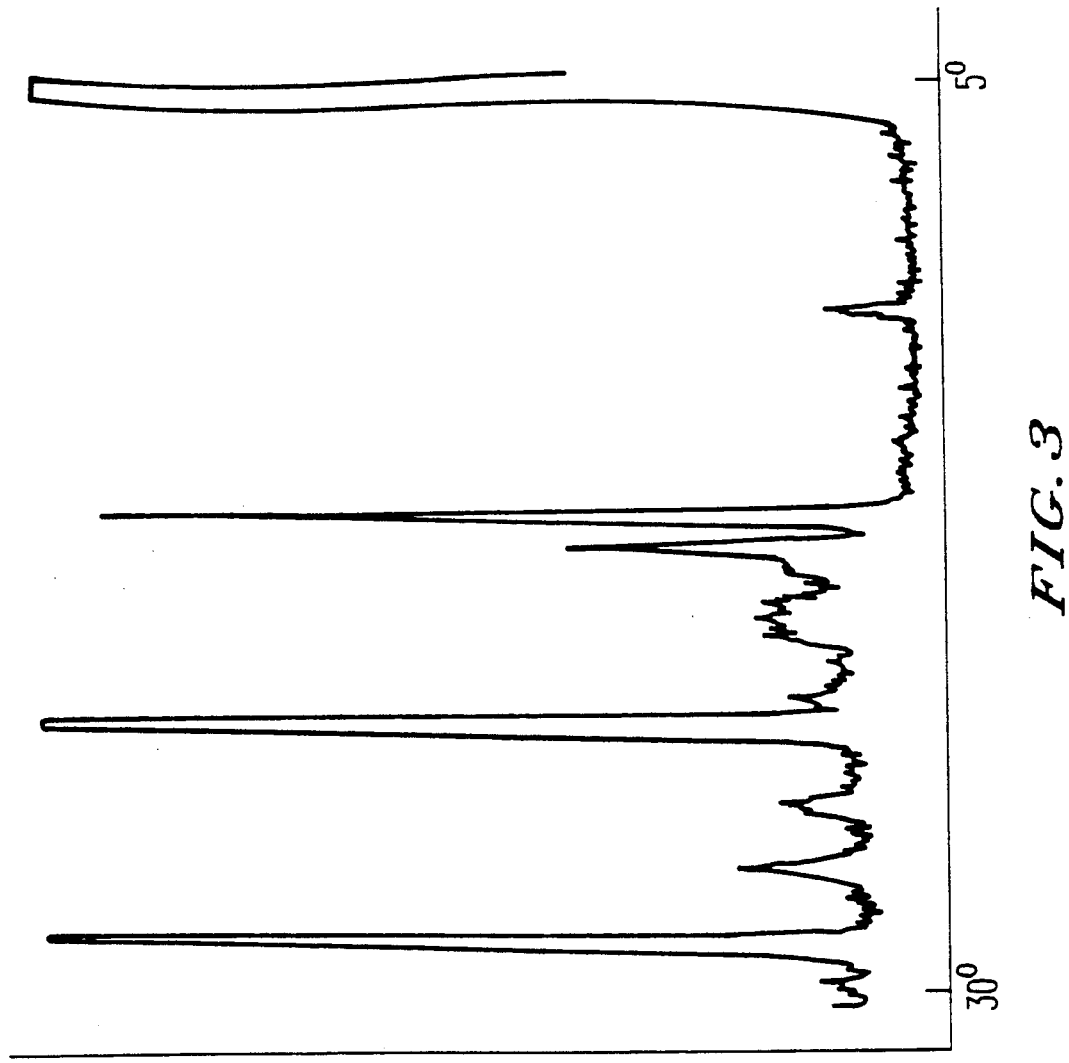
FIG. 3 is a powder X-ray spectra of the crystals obtained in Example 3.
Figure 4:
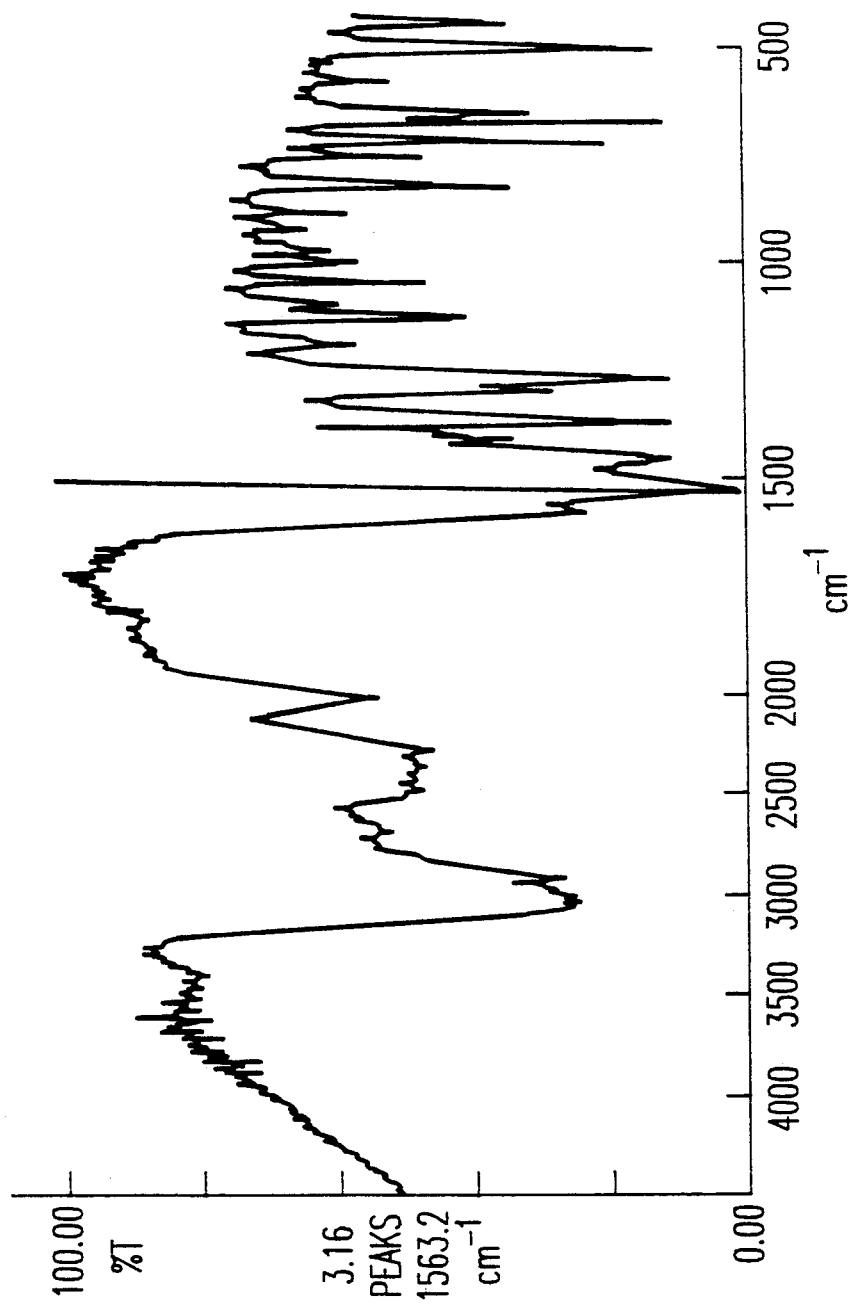
FIG. 4 is an IR spectra of the crystals obtained in Example 3.

A filter aid was added to an L-phenylalanine fermentation solution, the resulting mixture was filtered, the filtrate was concentrated at 60° C. under reduced pressure, the concentrate was gradually cooled to 38° C., and the crude crystals which separated out were collected. To 6 g of the crude crystals thus obtained, was added 100 ml water, the mixture was heated at 80° C. until a clear solution was obtained, and sodium chloride was then added to a concentration of 25 g/dl. The resulting solution was gradually cooled to 5° C. with stirring and allowed to stand overnight, the crystals which separated out were collected and washed with a small volume of water. The crystals thus obtained proved to be of α-crystal form by X-ray diffractometry (refer to Powder X-ray Chart FIG. 3 and IR Chart FIG. 4).

Yield from crude crystals: 5.42 g
Purity: 94.2% (measured by an amino-acid analyzer)
Rate of crystal separation: 85%

Example 4

| (Solution for Hydrolysis with HCl) | | |
|---|---|---|
| | Concn. | Amt. in 400 g |
| T—N | 1.41 M/L | |
| L—Phe | 11.4 g/dl | 0.069 M |

-continued

| (Solution for Hydrolysis with HCl) | | |
|---|---|---|
| | Concn. | Amt. in 400 g |
| L—Asp | 10.3 g/dl | 0.077 M |
| HCl | 3.9 M/l | |

To 100 ml of a solution containing L-phenylalanine of the above composition, was gradually added 48% aqueous solution of NaOH while maintaining the temperature at 80° C. until the pH reached 5.6, thus separating crystals of L-phenylalanine. The total amount of caustic soda solution added was 26 ml. The resulting mixture was gradually cooled to 5° C. with stirring and allowed to stand overnight, and the crystals were collected and washed with a small volume of water. The crystals thus obtained proved to be of α-crystal form.

Yield: 11.2 g
Purity: 94.7% (measured by an amino-acid analyzer)
Rate of Crystal Separation: 93%

Reference Example 1

Figure 5:
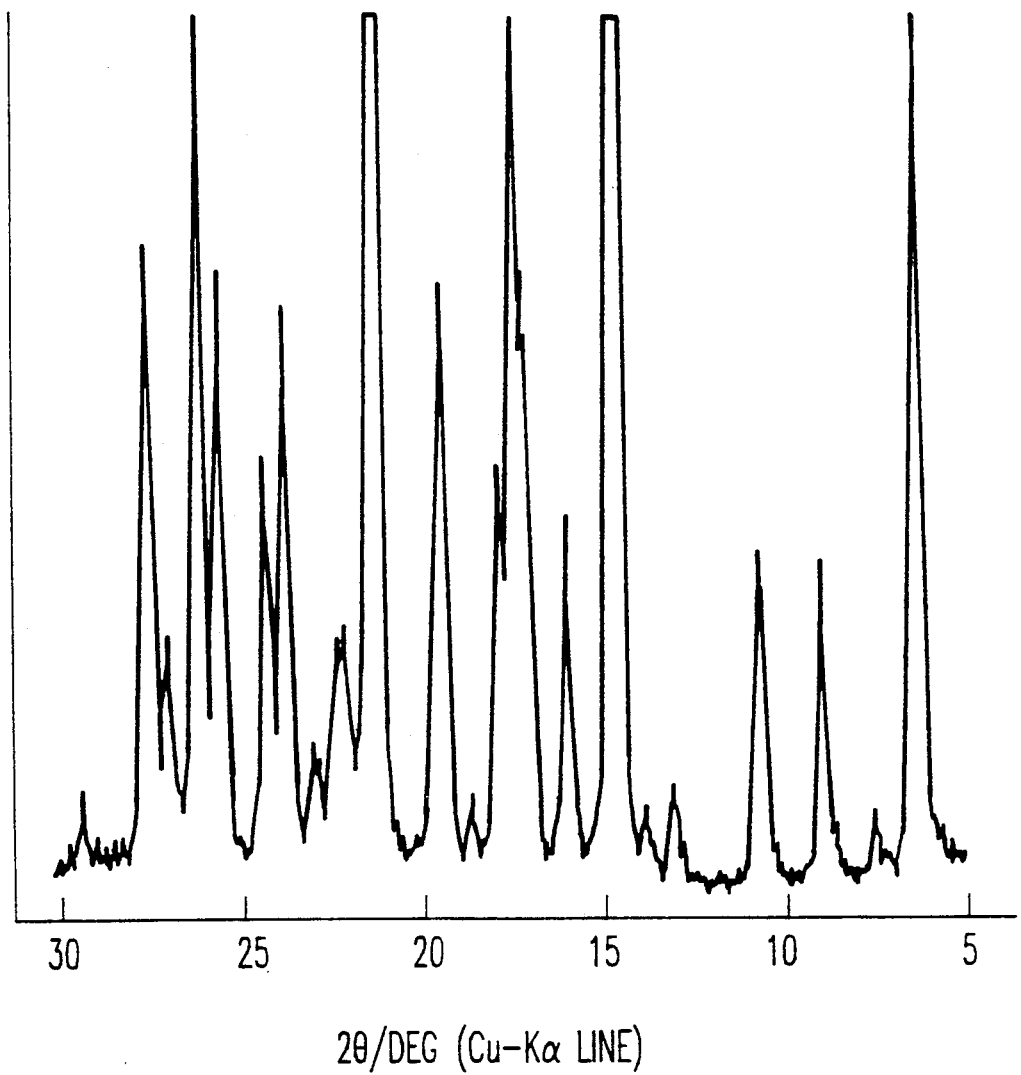
FIG. 5 is a powder X-ray spectra of the L-phenylalanine β-crystals obtained in Reference Example 1.
Figure 6:
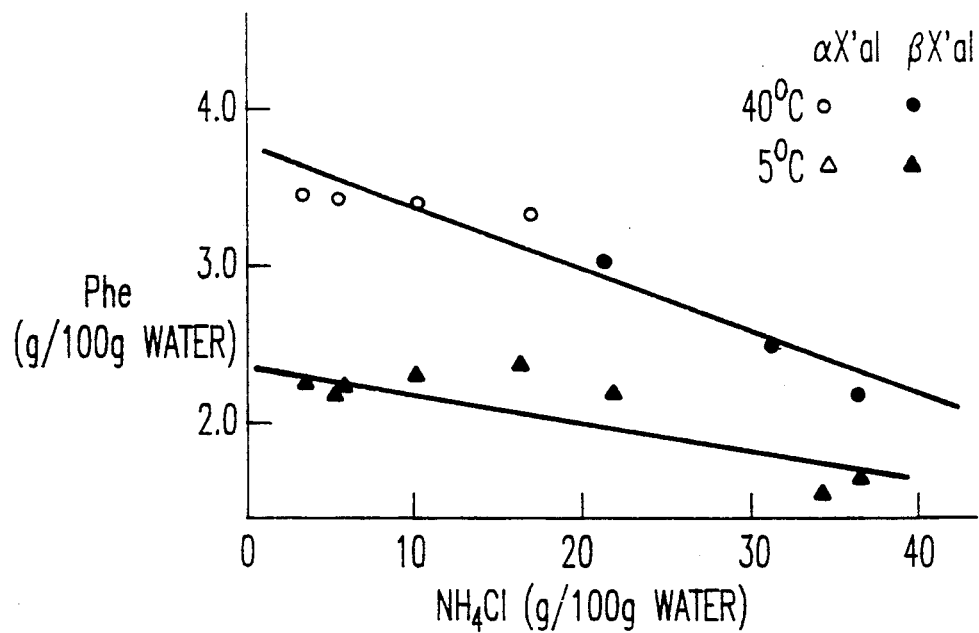
FIG. 6 is a graph showing the solubility and crystal form of L-phenylalanine in the presence of ammonium chloride at 40° C. and at 5° C. as a function of ammonium chloride concentration.
Figure 7:
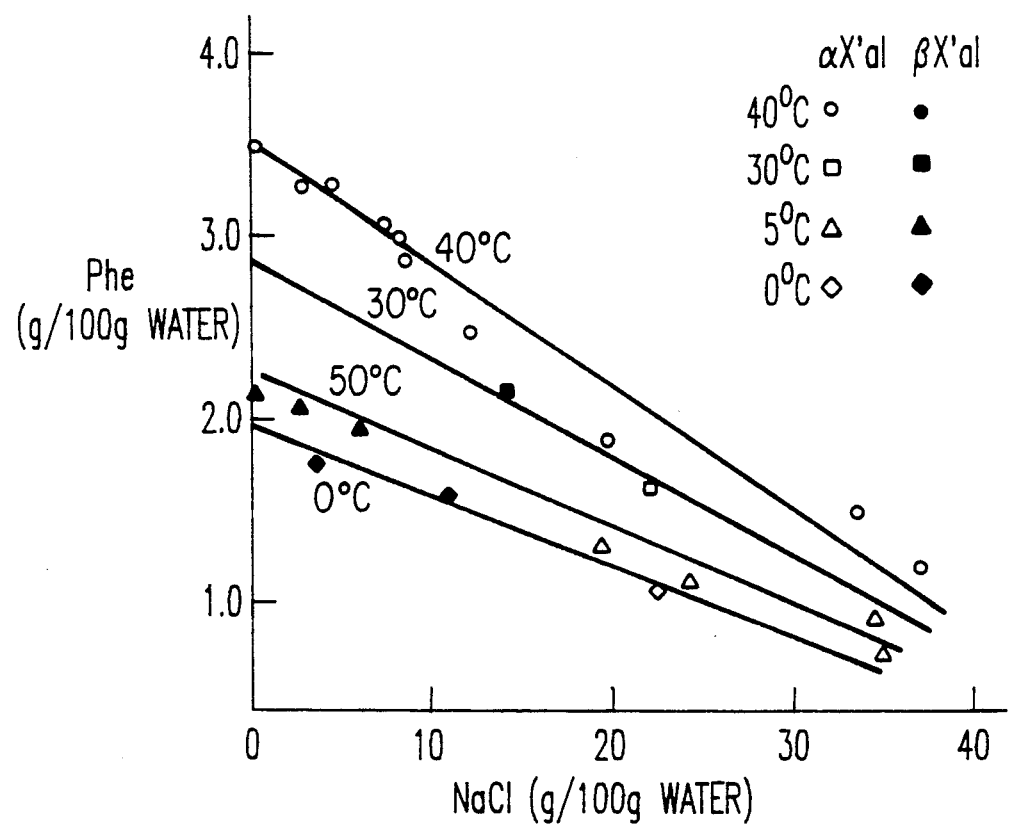
FIG. 7 is a graph showing the solubility and crystal form of L-phenylalanine in the presence of NaCl at 40° C., at 30° C., at 5° C. and at 0° C. as a function of NaCl concentration.

A solution containing L-phenylalanine of the same composition as in Example 1 was gradually cooled to 40° C. with no surface-active agent added thereto, and the crystals which separated out were collected. The crystals thus obtained proved to be of β-crystal form by observation under a microscope and by powder X-ray diffractometry (refer to Powder X-ray Chart FIG. 5).

Reference Example 2

To 400 g of a solution containing L-phenylalanine of the same composition as in Example 2, was gradually added ammonia water until the pH reached 5.6 with no surface-active agent added thereto, and the resulting mixture was gradually cooled. When the temperature was lowered to about 50° C., crystal-form transition occurred with the separated phenylalanine (α→β), thus making stirring impossible. Consequently, the crystals could not be satisfactorily isolated.

Reference Example 3

To 100 ml of a solution containing L-phenylalanine of the same composition as in Example 4, was gradually added 28% ammonia water while maintaining the temperature at 75° to 80° C. until the pH reached 5.6, thus separating crystals of L-phenylalanine, and the resulting mixture was gradually cooled with stirring. When the temperature was lowered to about 35° C., crystal-form transition occurred with the separated phenylalanine (α→β), thus making stirring impossible. Consequently, the crystals could not be satisfactorily isolated.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of crystallizing phenylalanine in the form of α-crystals at a temperature below the normal transition point temperature of phenylalanine, said normal transition point temperature being a temperature above which phenylalanine exists in the form of α-crystals and below which phenylalanine exists in the form of β-crystals, said method comprising:

forming an aqueous solution of phenylalanine at a temperature above said normal transition point temperature, said aqueous solution of phenylalanine including:
(1) at least 20 grams of sodium chloride per 100 grams of water in said solution, or
(2) ammonium chloride and a surface-active agent, said surface-active agent being present in an amount effective to suppress an increase in said normal transition point temperature brought about in an aqueous solution of phenylalanine by the presence of ammonium chloride in a concentration of about 20 grams per 100 grams of water in said solution;

cooling said aqueous solution of phenylalanine to a temperature below said normal transition point temperature to recover phenylalanine in said α-crystal form.

2. The method of claim 1, wherein said surface-active agent is non-ionic.

3. The method of claim 2, wherein said non-ionic surface active agent is a sorbitan alkyl ester or a polyoxyethylene sorbitan alkyl ester.

4. The method of claim 1, wherein said surface-active agent is present in an amount of at least 0.05% based on the weight of phenylalanine.

5. The method of claim 4, wherein said surface-active agent is present in an amount of from 0.05 to 0.5% based on the weight of phenylalanine.

* * * * *